(12) United States Patent
Meinhardt et al.

(10) Patent No.: US 6,430,966 B1
(45) Date of Patent: Aug. 13, 2002

(54) GLASS-CERAMIC MATERIAL AND METHOD OF MAKING

(75) Inventors: Kerry D. Meinhardt, Richland; John D. Vienna, West Richland; Timothy R. Armstrong, Pasco; Larry R. Pederson, Kennewick, all of WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/365,343

(22) Filed: Jul. 30, 1999

(51) Int. Cl.⁷ .............................. C03C 8/22; C03C 8/24
(52) U.S. Cl. ....................... 65/43; 65/36; 423/327.1; 423/328.1; 501/15; 501/21; 501/22; 501/24
(58) Field of Search ............................. 65/33.5, 33.6, 65/36, 43; 501/14, 15, 16, 21, 22, 24; 423/327.1, 328.1

(56) References Cited

U.S. PATENT DOCUMENTS

| | | | |
|---|---|---|---|
| 4,451,516 A | * 5/1984 | Kato | 428/116 |
| 4,585,972 A | * 4/1986 | Hing | 1/9 |
| 4,973,564 A | 11/1990 | Chyung et al. | 501/32 |
| 5,273,837 A | * 12/1993 | Aitken et al. | 429/30 |
| 5,453,331 A | 9/1995 | Bloom et al. | 429/32 |
| 5,479,700 A | * 1/1996 | Nachlas et al. | 29/825 |

FOREIGN PATENT DOCUMENTS

| | | | |
|---|---|---|---|
| EP | 0 351 097 A1 | * 1/1990 | |
| GB | 1019821 | * 2/1966 | |
| JP | 59-219850 | * 12/1984 | |

OTHER PUBLICATIONS

PH Larsen et al., "Stacking of Planar SOFCs", pp. 69–78. 1995 (No Month Available).

C Gunther et al., "The Stability of the Sealing Class AF 45 In $H_2/H_2O$—and $O_2/N_2$—Atmospheres", p. 746–756. 1997 (No Month Available).

KL Ley et al., "Glass–Ceramic Sealants for Solid Oxide Fuel Cells: Part I. Physical Properties", p. 1489–1493. J. Mater. Res. vol. 11, No. 6, Jun. 1996.

Y Sakaki et al., "Class–Ceramics Sealants in $CaO-Al_2O_2-SiO_2$ System", p. 652–660. 1997. ( No Month Available).

* cited by examiner

*Primary Examiner*—Sean Vincent
(74) *Attorney, Agent, or Firm*—Paul W. Zimmerman; Douglas E. McKinley, Jr.; Stephen R. May

(57) ABSTRACT

The present invention is a glass-ceramic material and method of making useful for joining at least two solid ceramic parts. The seal is a blend of $M_AO-M_BO_y-SiO_2$ that substantially matches a coefficient of thermal expansion of the solid electrolyte. According to the present invention, a series of glass ceramics in the $M_AO-M_BO_y-SiO_2$ system can be used to join or seal both tubular and planar ceramic solid oxide fuel cells, oxygen electrolyzers, and membrane reactors for the production of syngas, commodity chemicals and other products.

14 Claims, 1 Drawing Sheet

GLASS-CERAMIC MATERIAL AND METHOD OF MAKING

This invention was made with Government support under Contract DE-AC0676RLO1830 awarded by the U.S. Department of Energy. The Government has certain rights in the invention.

FIELD OF THE INVENTION

The present invention is a glass ceramic material and method of making, specifically for use in electrochemical devices such as fuel cells, gas sensors, oxygen or hydrogen pumps/separators or for sealing any material with expansion similar to the seal material.

As used herein, the terms "solid electrolyte" or "solid oxide ion conducting electrolyte" are interchangable.

As used herein, the term "joint" includes the term "seal" because, in this glass-ceramic field, the "seal" joins at least two parts. However, the "joint" may be intermittent thereby not serving as a "seal".

BACKGROUND OF THE INVENTION

Ceramic materials are being used more often from automobile turbochargers to experimental fuel cells. However, there remains the problem of joining and/or sealing between separate ceramic parts. For example, solid oxide ion conducting electrolytes are useful for oxygen separation and high temperature fuel cells. Although many technical challenges of their development have been overcome, there remains the problem of sealing. In a planar design, a gas-tight seal must bond the components together and prevent the mixing of the gas species on both sides of the solid oxide ion conducting electrolyte.

A limited number of materials are suitable as a solid oxide ion conducting electrolyte. The most commonly used materials are yttria stabilized zirconia, doped ceria, doped bismuth oxide and doped lanthanum gallate. The thermal expansion of these materials can range from $10.1 \times 10^{-6}$ to $14.3 \times 10^{-6}$ depending on the type of dopant and concentration. The operating temperature can also range from 700° C. to 1000° C. depending upon which material is chosen as the electrolyte. Therefore seal material must be tailored to match the electrolyte thermal expansion, maintain a gas tight seal at temperatures ranging from 200° C. to 1200° C., and not have detrimental chemical interactions with the cell components. In addition, the seal material must also be stable at the operating temperature (800–1000° C.) for extended periods of time (>9,000 hr) and be electrically insulating. For a solid oxide fuel cell the seal must be able to survive extremely reducing environments.

Various efforts to seal solid oxide ion conducting devices have been made with varying degrees of success. Silica, boron, and phosphate base glasses and glass-ceramics have been evaluated as a sealing material for solid oxide fuel cells. Experiments conducted by P. H. Larsen et al. have shown major problems with glasses purely based on phosphate as the glass former. At temperature, the phosphate volatilized and reacted with the anode to form nickel phosphide and zirconiumoxyphosphate. Additionally, these phosphate glasses usually crystallized to form meta- or pyrophosphates, which exhibited low stability in a humidified fuel gas at the operating temperature.

Borosilicate glasses and glass ceramics have also been considered as potential seal materials. These glasses have been investigated by C. Günther et al.[2] and K. L. Ley et al.[3] for use in solid oxide fuel cells. However, boron will react with a humidified hydrogen atmosphere to form the gaseous species $B_2(OH)_2$ and $B_2(OH)_3$ at the operating temperature[2]. Therefore, any high boron seal may corrode in a humidified hydrogen environment over time. Glasses with $B_2O_3$ as the only glass former have showed up to a 20% weight loss in the humidified hydrogen environment and extensive interactions with cell component materials both in air and wet fuel gas[1].

Silica based glasses and glass-ceramics offer the most promise. They typically have a higher chemical resistance and show minimal interaction with the cell component materials[1]. Unfortunately, these glasses tend to have thermal expansions below the range needed for a sealing material.

At the operating temperature, most glasses will crystallize with time. Therefore, it is critical to have a glass composition in which the thermal expansion coefficient after crystallization is compatible with the solid oxide ion conducting electrolyte. Once the glass is fully crystallized, it is typically very stable over time. In addition, crystallized glasses tend to be stronger mechanically at operating temperature, improving seal performance.

Hence, there is a need in the art for a sealing material that can operate at an operating temperature up to about 900° C., has a thermal expansion between $8 \times 10^{-6}$ and $15 \times 10^{-6}$ °C.$^{-1}$, and no detrimental chemical interactions with the components.

BACKGROUND REFERENCES

1. P. H. Larsen, C. Bagger, M. Mogensen and J. G. Larsen, *Proc. 4$_{th}$ Int. Symp. Solid Oxide Fuel Cells*, Volume 95-1, 1995, pp.69–78
2. C. Günther, G. Hofer and W. Kleinlein, *Proc. 5$^{th}$ Int. Symp. Solid Oxide Fuel Cells*, Volume 97-18, 1997, pp.746–756
3. K. L. Ley, M. Krumpelt, R. Kumar, J. H. Meiser, and I. Bloom, J. Mat. Res., Vol. 11, No. 6, (1996) pp. 1489–1493
4. Yoshinori Sakaki, Masatoshi Hattori, Yoshimi Esaki, Satoshi Ohara, Takehisa Fukui, Kaseki Kodera, Yukio Kubo, *Proc. 5$^{th}$ Int. Symp. Solid Oxide Fuel Cells*, Volume 97-18, 1997, pp.652–660

SUMMARY OF THE INVENTION

The present invention is a glass-ceramic compound and method of making that are useful in joining or sealing ceramic parts. More specifically, the present invention is useful for joining/sealing in an electrochemical cell having at least one solid electrolyte having a first and second side exposed to first and second gas species respectively. The seal is necessary for separating the first and second gas species.

The glass-ceramic compound contains at least three metal oxides, $M_AO_x$ —$M_BO_y$—$SiO2$. $M_A$ may be barium, strontium, calcium or a combination thereof. The combination of $M_AO_x$ and $SiO_2$ provides the desired thermal expansion coefficient, and $M_BO_y$ modifies the softening temperature. The compound substantially matches a coefficient of thermal expansion of the solid electrolyte.

According to the present invention, a series of glass ceramics in the $M_AO$—$M_BO_y$—$SiO_2$ system can be used to join or seal both tubular and planar ceramic solid oxide fuel cells, oxygen electrolyzers, and membrane reactors for the production of syngas, commodity chemicals and other products.

It is an object of the present invention to provide a compound useful for joining or sealing a solid electrolyte or a solid oxide ion conducting electrolyte.

An advantages of a seal made with the ternary compound of $M_AO_x$—$M_BO_y$—$SiO_2$ is the maintaining of a substantially constant coefficient of thermal expansion from the glass to crystalline phase.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

The present invention is a glass-ceramic compound and method of making the glass-ceramic compound. The present invention is useful for joining or sealing between at least two solid ceramic parts, for example a seal in an electrochemical cell having at least one solid electrolyte having a first and second side exposed to first and second gas species respectively. The seal is necessary for separating the first and second gas species during operation, usually at elevated temperatures.

The present invention includes a joint between at least two solid ceramic parts. The joint has at least three metal oxides of $M_AO_x$—$M_BO_y$—$SiO_2$ combined together wherein $M_A$ is selected from the group consisting of barium, strontium, calcium and combinations thereof. The joint substantially matches a coefficient of thermal expansion of the at least two solid ceramic parts. The subscripts x and y are integers varying from 1 to 5. The coefficient of thermal expansion of the joint is from about $7(10^{-6})°C.^{-1}$ to about $15(10^{-6})°C.^{-1}$ as measured from 25° C. to 1000° C.

The $M_BO_y$ provides a softening temperature of the $M_AO_x$—$M_BO_y$—$SiO2$ combination below the softening temperature of $M_AO_x$—$SiO2$. $M_BO_y$ includes but is not limited to $Al_2O_3$, $B_2O_3$, $P_2O_5$, $Ga_2O_3$, PbO and combinations thereof. Choice of $B_2O_3$ may be limited, especially for applications that have humid hydrogen environments. Choice of $P_2O_5$ may be limited to lower temperature applications and/or applications that do not include humid hydrogen environments.

Figure 1:
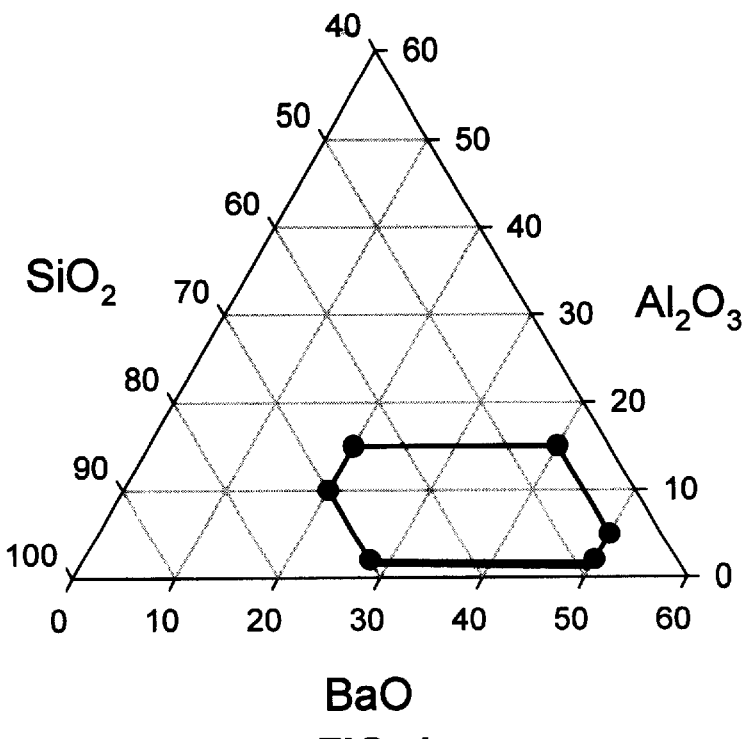
FIG. 1 is a phase diagram showing the compositional range of BaO—$Al_2O_3$—$SiO_2$ sealing materials according to the present invention.

The composition of the seal is preferably in the range wherein the $M_AO_x$ is present in an amount from about 20 mol % to about 50 mol %, the $M_BO_y$ is present in an amount from about 2 mol % to about 15 mol %, and the $SiO_2$ is present in an amount from about 45 mol % to about 70 mol %. This compositional range is shown in FIG. 1 for the ternary system of BaO—$Al_2O_3$—$SiO_2$.

The glass-ceramic compound may further contain at least one additional metal oxide including but not limited to SrO, $K_2O$, $B_2O_3$, CaO and combinations thereof to modify the properties of the glass phase or the final crystallized seal. Properties include but are not limited to wetting, glass transition temperature (Tg), glass softening temperature (Ts), thermal expansion coefficient and combinations thereof.

The range of thermal expansion coefficients for both glass-ceramic and crystallized glass-ceramic is from $7×10^{-6}$ to $13×10^{-6}$. The glass transition temperatures (Tg) and softening temperature (Ts) for the glasses are in the range of 650°–800° C. However, the crystallized glass has a softening temperature above 1000° C.

Substantially the same coefficient of thermal expansion is herein defined as the coefficient of thermal expansion of the seal material within about 30%, preferably within about 16%, more preferably within about 5% of the sealed material.

The joint may be used in an electrochemical test cell to join an oxygen ion pump and a test material. In addition, the joint may be used in an oxygen generator to join an oxygen ion conducting electrolyte, for example a zirconia electrolyte and an interconnect, for example manganite, metal and combinations thereof.

According to the present invention, a method of joining at least two solid ceramic parts has the steps of:

(a) providing a blend of $M_AO_x$, $M_BO_y$, and $SiO_2$ that substantially matches a coefficient of thermal expansion of said at least two ceramic parts, said $M_A$ selected from the group consisting of barium, strontium, calcium and combinations thereof;

(b) placing said blend at an interface of said at least two ceramic parts as a pre-assembly;

(c) heating said pre-assembly to a temperature sufficient to cause the blend to flow into and wet the interface as an assembly; and (d) cooling said assembly and solidifying said blend thereby joining said at least two ceramic parts.

EXAMPLE 1

An experiment was conducted to demonstrate the seal materials of the present invention.

Table E1-1 shows several compositions. The major crystallized phases can include $BaO•2SiO_2$, $2BaO•3SiO_2$, $BaO•SiO_2$, and $BaO•Al_2O_3•2SiO_2$.

TABLE E1-1

| Glass ID # | Seal Compositions | | | | | |
|---|---|---|---|---|---|---|
| | BaO | SrO | CaO | $K_2O$ | $Al_2O_3$ | $SiO_2$ |
| 1 | 34.8 | 4.8 | — | — | 10.4 | 50.0 |
| 3 | 33.0 | 5.0 | — | — | 7.7 | 54.3 |
| 7b | 33.7 | — | — | — | 10.5 | 55.8 |
| 9 | 36.9 | — | — | — | 10.5 | 52.6 |
| 10 | 42.5 | — | — | — | 7.5 | 50.0 |
| 11 | 45.0 | — | — | — | 5.0 | 50.0 |
| 12 | 41.3 | — | — | — | 5.0 | 53.7 |
| 13 | 37.5 | — | — | — | 5.0 | 57.5 |
| 1d | 34.8 | — | 4.8 | — | 10.4 | 50.0 |
| 1e | 34.8 | — | — | 4.8 | 10.4 | 50.0 |

Figure 2:
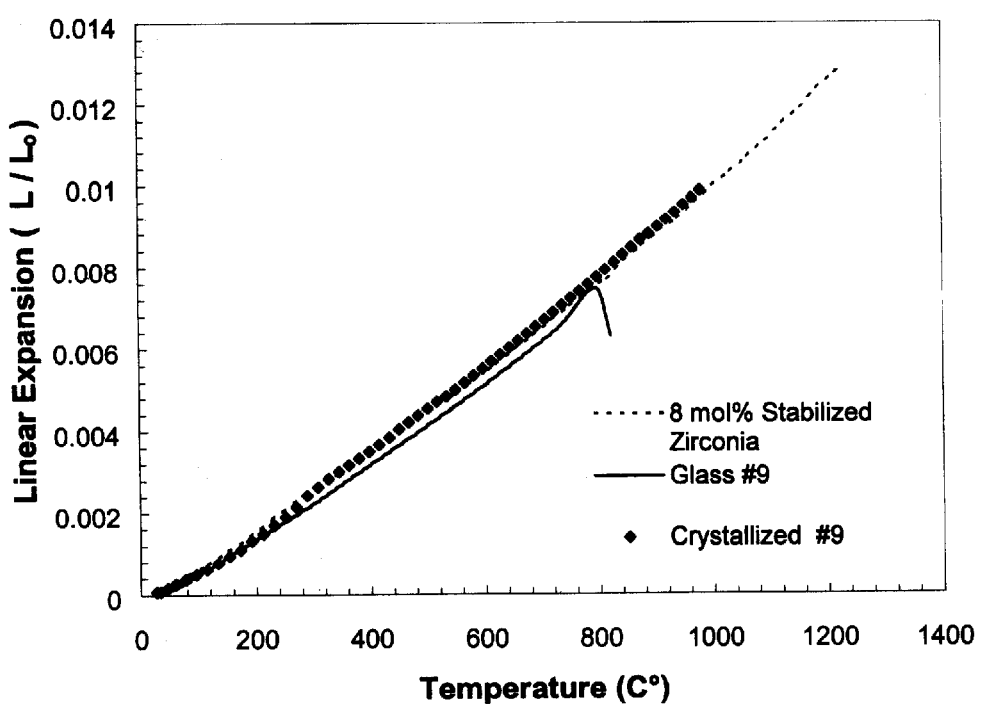
FIG. 2 is a graph of coefficient of thermal expansion versus temperature for a solid electrolyte, a glass and its crystallized phases of a substantially matching glass ceramic material.

FIG. 2 illustrates how well the seal material was tailored to match a solid electrolyte. The solid electrolyte material was 8-YSZ, and the glass composition was #9. The thermal expansion of the crystallized glass seal was within 0.06% of the expansion of the solid electrolyte material.

Table E1-2 shows glass properties.

TABLE E1-2

Seal Properties

| Glass ID # | Glass Transition Temperature (Tg, ° C.) | Softening Temperature (Ts, ° C.) | Thermal Expansion (Glass 25° C. to Tg) | Thermal Expansion (Crystallized Glass, 25° C. to 1000° C.) |
| --- | --- | --- | --- | --- |
| 1  | 700 | 760 | 10.3 | 12.8 |
| 3  | 728 | 791 | 9.5  | 9.2  |
| 7b | 760 | 803 | 8.8  | 7.6  |
| 9  | 726 | 803 | 9.4  | 10.5 |
| 10 | 736 | 788 | 11.2 | 13.4 |
| 11 | 710 | 763 | 11.4 | 14.6 |
| 12 | 702 | 749 | 11.5 | 12.8 |
| 13 | 695 | 745 | 11.1 | 9.6  |
| 1d | 738 | 802 | 10.0 | 11.5 |
| 1e | 720 | 783 | 10.4 | 12.5 |

EXAMPLE 2

Seals formed from a glass frit were used to fabricate sealed 8YSZ oxygen pumps. A zirconia pump of fully dense small closed end tube and test material of flat plate of 8 mol % stabilized zirconia were sealed together with a mixture of "Glass 9" from Example 1 to assemble an electrochemical test cell. The tube was electroded with Pt on both the inside and outside to function as an oxygen pump. Pt leads were connected to the electrodes. The pre-assembly was placed in a furnace, heated to 1150° C. to seal. The temperature was reduced after sealing to the crystallization temperature and held there until the seal crystallized. After crystallization, the assembly was allowed to cool to room temperature The assembly was tested by pumping oxygen out of the sealed assembly and found capable of reaching a partial pressure of oxygen of $1 \times 10^{-18}$ atms. at 1000° C. An oxygen leak rate of $3.7 \times 10^{-5}$ standard cubic centimeters per sec (sccs) was calculated from the pumping current. Although this is not considered a hermetic seal ($1 \times 10^{-19}$) it is adequate for solid oxide fuel cells and oxygen generators.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A joint between at least two solid oxide ceramic parts comprising: at least three metal oxides of $M_AO_X$—$M_BO_Y$—$SiO_2$ combined together wherein $M_A$ is selected from the group consisting of barium, strontium, calcium, and combinations thereof, and $M_BO_Y$ is selected from the group consisting of $Al_2O_3$, $B_2O_3$, $P_2O_5$, GaO, PbO and combinations thereof and contains over 5 mol % $Al_2O_3$ and provides a melting temperature of the $M_AO_X$—$M_BO_Y$—$SiO_2$ combination below the melting temperature of $M_AO_X$—$SiO_2$, said joint substantially matching a coefficient of thermal expansion of said at least two solid ceramic parts wherein said $M_AO_X$ is present in an amount from about 20 mol % to about 50 mol %, said $M_BO_Y$ is present in an amount from over 5 mol % to about 15 mol %, and said $SiO_2$ is present in an amount from about 45 mol % to about 70 mol %.

2. The joint as recited in claim 1 that is a seal.

3. The joint as recited in claim 1 wherein said coefficient of thermal expansion is from about $7(10^{-6})°$ C.$^{-1}$ to about $15(10^{-6})°$ C.$^{-1}$ as measured from 25° C. to 1000° C.

4. The joint as recited in claim 1, further comprising at least one additional metal oxide.

5. The joint as recited in claim 4, wherein said at least one additional metal oxide is selected from the group consisting of SrO, $K_2O$, $B_2O_3$, CaO and combinations thereof.

6. The joint as recited in claim 1, wherein said at least two ceramic parts are a oxygen ion pump and a test material in an electrochemical test cell.

7. The joint as recited in claim 1, wherein said at least two ceramic parts are a oxygen ion conductor and an interconnect in an oxygen generator.

8. A method of joining at least two solid ceramic parts, comprising the steps of:

(a) providing a blend of $M_AO_X$, $M_BO_Y$, and $SiO_2$ that substantially matches a coefficient of thermal expansion of said at least two solid ceramic parts, said $M_A$ selected from the group consisting of barium, strontium, calcium, and combinations thereof and $M_BO_Y$ is selected from the group consisting of $Al_2O_3$, $B_2O_3$, $P_2O_5$, GaO, PbO and combinations thereof and contains over 5 mol % $Al_2O_3$;

(b) placing said blend at an interface of said at least two ceramic parts as a pre-assembly;

(c) heating said pre-assembly to a temperature sufficient to cause the blend to flow into said interface as an assembly and (d) cooling said assembly and solidifying said blend thereby joining said at least two ceramic parts wherein said $M_AO_X$ is present in an amount from about 20 mol % to about 50 mol %, said $M_BO_Y$ is present in an amount from over 5 mol % to about 15 mol %, and said $SiO_2$ is present in an amount from about 45 mol % to about 70 mol %.

9. The method as recited in claim 8 wherein said joining is sealing.

10. The method as recited in claim 8 wherein said coefficient of thermal expansion is from about $7(10^{-6})°$ C.$^{-1}$ to about $15(10^{-6})°$ C.$^{-1}$ as measured from 25° C. to 1000° C.

11. The method as recited in claim 8, further comprising at least one additional metal oxide.

12. The method as recited in claim 11, wherein said at least one additional metal oxide is selected from the group consisting of SrO, $K_2O$, $B_2O_3$, CaO and combinations thereof.

13. The method as recited in claim 8, wherein said at least two ceramic parts are a oxygen ion pump and a test material in an electrochemical test cell.

14. The method as recited in claim 8, wherein said at least two ceramic parts are a oxygen ion conductor and an interconnect in an oxygen generator.

* * * * *